(12) United States Patent
Habar

(10) Patent No.: US 10,399,056 B2
(45) Date of Patent: Sep. 3, 2019

(54) PROCESS FOR MANUFACTURING DOUBLE-WALLED MICROCAPSULES, MICROCAPSULES PREPARED BY THIS PROCESS AND THE USE THEREOF

(71) Applicant: MICROCAPSULES TECHNOLOGIES, Puiseau (FR)

(72) Inventor: Gerard Daniel Habar, Bourron-Marlotte (FR)

(73) Assignee: MICROCAPSULES TECHNOLOGIES, Puiseau (FR)

( * ) Notice: Subject to any disclaimer, the term of this patent is extended or adjusted under 35 U.S.C. 154(b) by 0 days.

(21) Appl. No.: 15/110,521

(22) PCT Filed: Dec. 4, 2014

(86) PCT No.: PCT/FR2014/053165
§ 371 (c)(1),
(2) Date: Jul. 8, 2016

(87) PCT Pub. No.: WO2015/104469
PCT Pub. Date: Jul. 16, 2015

(65) Prior Publication Data
US 2016/0325259 A1    Nov. 10, 2016

(30) Foreign Application Priority Data

Jan. 10, 2014   (FR) ..................... 14 50166

(51) Int. Cl.
| | |
|---|---|
| *A61K 8/11* | (2006.01) |
| *B01J 13/14* | (2006.01) |
| *B01J 13/22* | (2006.01) |
| *C11D 3/50* | (2006.01) |
| *A01N 25/28* | (2006.01) |
| *A61K 8/893* | (2006.01) |
| *A61Q 5/02* | (2006.01) |
| *A61Q 5/12* | (2006.01) |
| *A61Q 11/00* | (2006.01) |
| *A61Q 19/00* | (2006.01) |
| *A61Q 19/10* | (2006.01) |
| *C11B 9/00* | (2006.01) |

(52) U.S. Cl.
CPC .............. *B01J 13/14* (2013.01); *A01N 25/28* (2013.01); *A61K 8/11* (2013.01); *A61K 8/893* (2013.01); *A61Q 5/02* (2013.01); *A61Q 5/12* (2013.01); *A61Q 11/00* (2013.01); *A61Q 19/007* (2013.01); *A61Q 19/10* (2013.01); *B01J 13/22* (2013.01); *C11B 9/0034* (2013.01); *C11D 3/505* (2013.01); *A61K 2800/56* (2013.01)

(58) Field of Classification Search
None
See application file for complete search history.

(56) References Cited

U.S. PATENT DOCUMENTS

| 2011/0200654 A1* | 8/2011 | Habar ...................... A61K 8/11 424/401 |
| 2014/0221202 A1 | 8/2014 | Boday et al. |
| 2014/0227329 A1 | 8/2014 | Habar |

FOREIGN PATENT DOCUMENTS

| CN | 101530766 | 9/2009 |
| CN | 102079970 | 6/2011 |
| WO | WO2008/009216 | 1/2008 |
| WO | WO-2011161618 A1 * | 12/2011 ............... A61K 8/11 |

OTHER PUBLICATIONS

Sauca, S.N.; Zhang, Z.; Novel Double-Shell Microcapsules, Mar. 2013, Bioencapsulation Research Group, pp. 26-27. (Year: 2013).*
Search Report dated Mar. 30, 2015.
Chinese Office Action dated May 3, 2017 w/ English Translation.

* cited by examiner

*Primary Examiner* — Jessica Worsham
(74) *Attorney, Agent, or Firm* — IPSILON USA, LLP

(57) ABSTRACT

Process for manufacturing reservoir microcapsules containing an active principle in a polymer shell comprising the steps of: (iii) dispersion of a lipophilic active principle in an aqueous continuous phase, forming an oil-in-water emulsion, (iv) introduction into the lipophilic phase of one or more compounds A bearing alkoxysilane groups, (v) introduction into the aqueous phase of amine-containing organic monomers B comprising at least one group selected from melamine, urea, glycoluril, benzoguanamine or dicyandiamide groups and one or more aldehydes, or pre-polymers thereof and (vi) hydrolysis and polymerization, in situ, of the compounds A and B in an acid medium to give a silicone polymer and an amine-containing polymer, bonded together by polar, hydrogen or covalent bonds, forming the wall of the shell of the microcapsules, containing the active principle. Microcapsules containing a lipophilic active agent, the double-walled shell of which is formed from two polymers, one being a silicone copolymer, the other an amine-containing organic polymer, and use of these microcapsules in formulations comprising surfactants.

18 Claims, No Drawings

US 10,399,056 B2

PROCESS FOR MANUFACTURING DOUBLE-WALLED MICROCAPSULES, MICROCAPSULES PREPARED BY THIS PROCESS AND THE USE THEREOF

RELATED APPLICATIONS

This application is a National Phase Application of PCT/FR2014/053165 filed on Dec. 4, 2014, which in turn claims the benefit of French Patent Application No. 14 50166, filed on Jan. 10, 2014 the entirety of which are incorporated herein by reference.

BACKGROUND

Field of the Invention

The present invention relates to a process for manufacturing reservoir microcapsules, the microcapsules thus produced and the use thereof in formulations such as washing agents.

The microcapsules called reservoir microcapsules (also called core/shell microcapsules) are microcapsules of the type containing an active ingredient in a polymer-based envelope.

The processes for manufacturing these microcapsules, and therefore for incorporating the active ingredient in a polymer, comprise the steps consisting of:
  dispersing at least one lipophilic, or hydrophilic, active ingredient in an aqueous continuous phase or an organic continuous phase, so as to form an emulsion or a dispersion of droplets of the oil-in-water or water-in-oil type, respectively,
  polymerizing a precursor of the polymer in situ at the periphery of said droplets to form the wall of the envelope of the microcapsules, enclosing the active ingredient.

Prior Art

Most of the encapsulation processes employed industrially nowadays concern processes involving polymerization of aminated monomers or of aminated organic prepolymers in the presence of aldehyde(s). The processes such as those described notably in U.S. Pat. No. 4,406,816 of BASF, U.S. Pat. No. 4,824,823 of KOEHLER, or U.S. Pat. No. 4,396,670 of WIGGINS TEAPE use melamine-formaldehyde resins, which give microcapsules that are impervious but are not resistant in the presence of detergents.

Another drawback of these microcapsules is their high residual formaldehyde content, despite the various treatments that have been developed for reducing its level, such as the treatments disclosed in documents EP 1797947 or U.S. Pat. No. 7,968,510.

For lowering the residual formaldehyde content, various copolymers have been proposed, such as those described in patent application US 2010/0009893.

Finally, aminated resins manufactured without formaldehyde and intended for encapsulation have been described, such as in patent applications US 2010/0247941 or WO/2011/161618, without improving the resistance to surfactants.

Other processes employing monomers of the silicate or silicone type have been proposed, notably in patent FR 2937248, for making the envelope of the microcapsules. However, these microcapsules are difficult and expensive to manufacture and do not offer satisfactory resistance to surfactants.

The major drawback of all these microcapsules of the prior art is lack of hermeticity of the polymer envelope, notably when the microcapsules are brought into contact with surfactants, notably in formulations such as washing agents, shampoos, or detergents for example. In fact surfactants are known to be "microcapsule killers" as they extract the constituents that are inside the microcapsules and release them.

Multilayer encapsulation processes have been developed based on aminated monomers or aminated organic prepolymers, to reinforce the hermeticity of the envelope, but these processes have to be carried out in several steps, and notably do not solve the question of hermeticity in the presence of surfactants.

A first aim of the invention is to propose a process for manufacturing reservoir microcapsules allowing an active substance to be incorporated in a polymer envelope having better hermeticity to surfactants than the microcapsules of the prior art.

Another aim of the invention is to propose a process for manufacturing reservoir microcapsules having a low content of residual aldehyde(s).

Another aim of the invention is to propose a process for incorporating an active ingredient of the perfume type in a suspension or dispersion of reservoir microcapsules intended to be used in formulations containing surfactants.

These aims are achieved by the process according to the present invention, which relates to a process for manufacturing reservoir microcapsules (in aqueous suspension), of the type containing an active ingredient in a polymer-based envelope comprising the steps consisting of:
  (i) dispersing at least one lipophilic active ingredient in an aqueous continuous phase, so as to form an emulsion or a dispersion of droplets of the oil-in-water type,
  (ii) polymerizing at least one precursor of the polymer in situ at the periphery of said droplets to form the wall of the envelope of the microcapsules, enclosing the active ingredient,
  characterized in that
  the polymerization step (ii) is preceded by the introduction of one or more compounds A bearing alkoxysilane groups into the lipophilic phase and the introduction of aminated organic monomers B into the aqueous phase, comprising at least one group selected from the melamine, urea, glycoluril, benzoguanamine, or dicyandiamide groups and one or more aldehydes, and/or prepolymers thereof.
  compounds A and B then being, preferably simultaneously, respectively hydrolyzed and condensed in an acid medium to a silicone polymer and an aminated organic polymer, bound together by polar, hydrogen or covalent bonds, making up the wall of the envelope of the microcapsules.

The silicone polymers and the aminated organic polymers are known to be incompatible, and no process of the prior art for multilayer encapsulation combines these two types of polymers. Surprisingly, the process according to the present invention not only allows incompatible polymers to be used together, but in addition polymerize them simultaneously or almost simultaneously if compounds B are introduced with a slight delay to give formation of the silicone polymer a slight lead. This simple process thus allows easy encapsulation of a lipophilic active substance in a double-walled composite envelope: a silicone polymer wall surrounded by a wall of aminated organic polymer.

DESCRIPTION OF THE INVENTION

Encapsulation envelopes of this kind thus combine the properties of the silicone membranes with that of the organic membranes and lead to a barrier effect far greater than the effect provided by each of them, said barrier effect being greatest when the microcapsules are used notably in the presence of chemicals such as surfactants.

Another advantage of the process according to the present invention is that it lowers the final aldehyde content owing to the constitution of the polymer envelope, namely that the aminated polymer only represents one part of the envelope of the microcapsules.

In fact it is noted that the level of residual formaldehyde, compared to that of conventional encapsulation by polymerization of melamine-formaldehyde or urea-formaldehyde resin, is considerably reduced precisely because of the smaller amount of melamine-formaldehyde or urea-formaldehyde resin used, since a portion is replaced by a silicone polymer, but also because the silicone resin does not retain the formaldehyde. This is a great, advantage of this type of microcapsules in a large number of applications, compared to the melamine microcapsules currently in use.

Moreover, the use of two different polymers for making said envelope of the microcapsules makes it possible, by varying their respective proportions, to make microcapsules to measure, adapted as far as possible to their final environment, as well as optionally to provide the whole structure with good mechanical performance by chemical reactions bonding the two types of polymers.

The process of the invention also offers the advantage of manufacturing "reservoir" microcapsules from inexpensive, widely-available monomers that are the precursors of the polymer of the silicone type, while employing a general encapsulation technique that is moreover already known by a person skilled in the art for the aminated organic polymer.

Preferably, the two polymers, silicone and aminated organic, are formed simultaneously by acid catalysis at a pH between 2 and 6.

In fact, addition of an acid catalyzes not only polymerization of the aminated resin, but also hydrolysis of the groups SiOR to SiOH as well as their subsequent reaction: 2 SiOH→Si—O—Si+H$_2$O. Surprisingly, and this is one of the key points of this invention, it was found that the acids usually employed for polymerization of the aminated resins such as formic, hydrochloric, sulfuric, nitric, or sulfonic acid were also able to polymerize the silicone polymer simultaneously in the conditions of pH between 2 and 6 and at a suitable temperature so as to allow hydrolysis of the groups Si—O—R before the organic membrane becomes too impermeable to water.

Advantageously, the two polymers, silicone and aminated organic, are formed simultaneously by acid catalysis at a pH between 3 and 5, by adding at least one acid comprising nitric acid to the oil-in-water emulsion or dispersion. This acid is in fact a very good catalyst of the hydrolysis and subsequent polymerization of the siloxane groups, and moreover it proves to be compatible with polymerization of the aminated resins.

According to a preferred embodiment, of the invention, the aminated organic prepoiymer is a melamine-formaldehyde and/or urea-formaldehyde resin. This type of prepolymer has the advantage of being readily available industrially and inexpensive, and its polymerization is well described and is known by a person skilled in the art. However, the presence of formaldehyde may prove prohibitive in many applications. In these applications it is then preferable, for manufacturing the aminated organic polymer, to use an aldehyde other than formaldehyde, namely an aldehyde advantageously selected from acetaldehyde, glyoxal, glutaraldehyde, or a mixture thereof, and/or one or more acetals of these aldehydes.

Melamine and/or urea may also preferably be used with these aldehydes other than formaldehyde, but it, is also possible for reasons of reaction kinetics or final performance to replace them completely or partially with another known aminated molecule such as glycoluril and/or benzoguanamine and/or dicyandiamide for example, to react with the aldehydes and lead to polymers possessing good performance.

The aminated resin without formaldehyde may also be prepared from the monoacetals or diacetals of these same aldehydes, or from the mixture of aldehydes and acetals; it can be esterified, and crosslinked by polymers bearing hydroxyl, mercapto, carboxylic acid, amine, or amide groups whether they are aromatic such as the phenols and derivatives thereof bearing carboxylic acid or sulfonic groups, or aliphatic such as monosaccharides and cellulose derivatives.

Replacement of the melamine-formaldehyde or urea-formaldehyde resins with a resin without formaldehyde is simpler to accomplish in the process according to the present invention than in the case of polymerization in situ of an aminated resin alone because the structure of the microcapsule is based in part on the polymer of the silicone type and the aminated polymer may only represent a small portion of the wall of the microcapsule. In these conditions it is not necessary to produce a prepoiymer with the aldehydes and the aminated molecules as is the case in the techniques described previously, but it is possible to synthesize the aminated organic polymer directly in the aqueous phase by introducing separately the aldehydes or the acetals thereof and the aforementioned aminated molecules such as melamine, urea etc., which is a considerable economic advantage as it, eliminates one step in the execution of the process.

As a variant the aminated organic polymer may be copolymerized with aliphatic or aromatic hydroxylated monomers and/or aromatic aldehydes, which may prove desirable for further increasing the hermeticity of the microcapsules and their resistance to surfactants.

Preferably the compound or compounds A bearing alkoxysilane functions is/are selected from the compounds of formula (I) or (II) below:

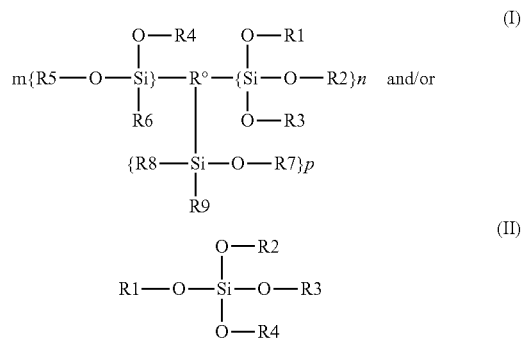

in which R1, R2, R3, R4, R5, R6, R7, R8, R9 are substituted or unsubstituted, linear or cyclic alkyl radicals, R° is an organic and/or silicone molecule, the groups between { } being joined to R° by a silicon atom and are present m, n, or p times, and m, n, p may be zero individually, but the sum m+n+p is at least equal to 1.

As examples, the monomers or prepolymers (I) usable for synthesizing the silicone polymer may be selected from the following nonexhaustive list:

monomers or prepolymers of trialkoxysilane R—Si(OR')$_3$ in which R represents an alkyl radical with 1 to 20 carbon atoms, substituted or unsubstituted, such as for example the radicals methyl, ethyl, n-propyl, isopropyl, 1-n-butyl, 2-n-butyl, isobutyl, tert-butyl, n-pentyl, isopentyl, neopentyl, tert-pentyl, hexyl such as n-hexyl, heptyl such as n-heptyl, octyl such as n-octyl or isooctyl, 2,2,4-trimethyipentyl, nonyl, decyl, dodecyl, or octadecyl;

R may also be a cyclic, cycloalkyl radical such as cyclopentyl, cyclohexyl, cycloheptyl and methylcyclohexyl, also an aryl radical such as phenyl, naphthyl, anthryl and phenanthryl, or an alkaryl radical such as o-, m- or p-tolyl, xylyl and ethylphenyl, or an aralkyl radical such as benzyl, alpha- and beta-phenylethyl;

R may also be halogenated such as for example 3,3,3-trifluoro-n-propyl, 2,2,2,2',2',2'-hexafluoroisopropyl, heptafluoroisopropyl, o-, m- or p-chlorophenyl;

R may be an unsaturated radical such as the vinyl, 5-hexenyl, 2,4-divinylcyclohexylethyl, 2-propenyl, allyl, 3-butenyl, 4-pentenyl, ethynyl, propargyl and 2-propynyl radicals;

R may also bear reactive groups capable of reacting with the organic polymer, such as the groups NH, OH, COOH, epoxide, urea or SH.

Some interesting monomers are mentioned below as nonlimiting examples, including:

chlorinated silanes such as chloropropylmethyldimethoxysilane, silanes bearing isocyanate groups such as propyltriethoxysilane isocyanate, epoxides such as glycidoxy propyltrimethoxy or triethoxysilane, glycidoxy propylmethyldiethoxysilane, (3,4-epoxycyclohexyl)ethyltrimethoxy or triethoxysilane, acrylic silanes: acryloxypropyltrimethoxysilane, methacryloxypropyltrimethoxysilane, gamma-methacryloxypropylmethyl dimethoxy- or diethoxysilane, silanes bearing thiol groups or sulfur atoms: mercaptopropylmethyl dimethoxysilane, bis-{3-(triethoxysilyl)propyl} polysulfide, bis-{3-(triethoxysilyl)propyl} disulfide, 3-octanoylthio-1-propyl triethoxysilane, aminated silanes: 3-aminopropyltriethoxy- or methoxysilane, N-(n-butyl)-3-aminopropyl trimethoxy- or ethoxysilane, N-aminoethyl-3-aminopropylmethyl dimethoxysilane, N-aminoethyl-3-aminopropyl trimethoxy- or triethoxysilane, 3-aminopropylmethyl diethoxysilane, N-phenylaminopropyl trimethoxysilane, 2-aminoethylaminopropyl trimethoxysilane, 2-aminoethylaminopropylmethyl dimethoxysilane, anilinopropyl trimethoxysilane, gamma-[N-(beta-aminoethyl)amino] propylmethyl dimethoxysilane, 4-amino-3,3-dimethylbutyl trimethoxysilane, 4-amino-3,3-dimethylbutylmethyl dimethoxysilane, bis-{gamma-(trimethoxysilyl)propyl}amine, N-ethyl-gamma-aminoisobutyl trimethoxysilane, 3-ureidopropyl triethoxysilane, hexamethyldisilazane, alkylene oxide trimethoxysilane, Tris-{3-(trimethoxysilyl)propyl} isocyanurate, bis(triethoxysilyl)ethane.

The choice is very wide, which makes this technology very malleable and versatile and makes it possible to manufacture microcapsules "to measure", which can be adapted to their final use.

R' is generally an alkyl radical, preferably short-chain, such as the methyl and ethyl radicals, which have higher reaction rates, or else a radical bearing an oxygen atom, for example selected from the methoxyethyl, ethoxyethyl, acetoxy or oximino radicals, or an alkyl radical bearing a halogen atom, chlorine being preferred.

Monomers such as monoalkoxysilane or dialkoxysilane intended to decrease the degree of crosslinking and thus make the silicone polymer pliable are also interesting.

It is of course possible, and interesting depending on the final uses envisaged for the microcapsules, to employ monomers in the process according to the present invention that are more complex than those mentioned above, such as:

tris-alkoxyisocyanurates, bis-alkoxysilanes, adducts such as those described in French patent FR 2,913,887, those obtained by reacting together silanes bearing reactive groups such as glymo (3-glycidoxypropyl) trimethoxysiiane) with an aminated silane such as 3-aminopropyitriethoxysilane, glymo with a mercaptosilane, a mercaptosilane with an isocyanato propyl triethoxysilane, isocyanato propyl triethoxysilane with 3-aminopropyltriethoxysilane, etc. These adducts have the advantage of offering a higher polymer/monomer weight ratio than the classical siloxanes, which reduces the amount of alcohol released and of water consumed per unit, weight of silicone polymer formed. This is an advantage, bearing in mind that the hydrolysis and the departure of alcohol that results from polymerization of the silicone are hampered by the aminated polymer forming around the microcapsules. Thus, by reducing the amount of these products migrating to the oil/water interface, the efficiency of the polymerization reactions of the silicone polymer and the reaction rate are increased, compounds obtained by reaction of a hydrocarbon-containing molecule bearing reactive groups reacting with the reactive groups present in the carbon chain of the organosiloxane, for example those obtained by reaction of an organic epoxide with an aminated silane, or those obtained by reaction of an organic polyisocyanate with MTMO (3-mercaptopropyltrimethoxysilane), or those obtained by reaction of an organic polythiol with glymo. The latter category of molecule has the advantage of being more compatible with the aminated organic polymer.

Regarding the nature of the molecule of the silicate (II) type that may be used alone or combined with the silicone structure, the monomers and prepolymers of the silicic ester type Si(OR')$_4$ (in which R' has the same meaning as the groups described above) also give good results, in particular the methyl and/or ethyl polysilicates, which are very commonly used and are inexpensive, and have the particular feature that they are very lipophilic and therefore do not diffuse in the aqueous phase even when they are completely hydrolyzed.

According to an advantageous embodiment of the process of the present invention, the compound of formula (II) is therefore selected from methyl polysilicate, ethyl polysilicate or a mixture thereof.

The above list, is not limiting: it may also include the oligomers of these products. One of the important criteria is that the compound bearing the alkoxysilane groups remains liquid and at least partially soluble, or dispersible, in the lipophilic phase, and preferably insoluble in the aqueous phase.

It can therefore be seen that there are countless possibilities, allowing fine adjustment of the properties of the membrane of the microcapsule, notably its permeability and its resistance to external chemical agents, such as surface-active compounds.

In one of the simplest embodiments, the hydrolyzable polymers bearing groups Si—O—R, namely ethyl polysilicate and optionally a mixture of methyltriethoxysilane and silanes possessing one or more groups capable of reacting with the aminated organic resin used, are introduced with stirring into the lipophilic phase containing the active substance, the phase that will become the internal phase of the microcapsules after dispersion in water. In the common case where a melamine-formaldehyde or urea-formaldehyde resin is used in the aqueous phase, a proportion of the silanes will usefully bear, on their nonhydrolyzable moiety, groups such as OH, SH (MTMO for example) epoxide (glymo for example) or urea (ureidopropyltrimethoxysilane for example). It is stirred until the reaction mixture is homogeneous and transparent. The type of silane or of silicate and their proportion is of course to be selected so that these products are sufficiently soluble in the lipophilic phase, so as to obtain as far as possible, but this is not imperative, a transparent solution favorable for construction of the walls of the microcapsule.

This lipophilic phase thus constituted, which is generally intended to become the internal phase of the microcapsules, is dispersed in water containing the usual polymers and protective colloids necessary for construction of the polymer of aminated resin. If applicable, some of the silicates or silane, among others those capable of reacting on the aminated resin, may be introduced into the aqueous phase. It should be noted that in any case the aminated resin reacts at least partially on the silanol groups if the conditions are suitable.

Once again, unexpectedly and surprisingly simply, introduction of acid causes deposition of the polymer by polymerization of the arnine-aldehyde prepolymer, at the same time that simultaneous polymerization of the silicone takes place at the interface in contact with water. Everything happens at the beginning as if the forming aminated polymer played the role of protective colloid with respect to formation of the microcapsules with a silicone wall, which is particularly unexpected.

The next operations, such as cooling, increase in pH, treatment with the aim of decreasing the level of residual formaldehyde when it is present, addition of preservatives, thickeners etc., are conventional and therefore familiar to a person skilled in the art.

The so-called silicone polymer and the organic polymer then form the composite double wall of the envelope of the microcapsule in very variable proportions. The interesting effects obtained notably on the possible level of residual formaldehyde, on the hermeticity and on the resistance to surfactants, occur when the silicone polymer represents advantageously from 5 to 95%, preferably from 10 to 90%, more preferably from 15 to 85%, of the total weight of the polymers forming the wall of the microcapsule.

Around a silicone polymer/aminated polymer weight ratio close to 10/90, microcapsules of aminated polymer are obtained that are improved by a thin inner layer of silicone, and around a silicone polymer/aminated polymer weight ratio close to 90/10, silicone microcapsules protected by a thin layer of aminated polymer. Between these two extremes, a whole range of microcapsules may be manufactured, adapted to their environment of final use.

As is well known by a person skilled in the art, formation of the emulsion and maintenance of its integrity during encapsulation are promoted by introducing a water-soluble polymer into the aqueous continuous phase, called protective colloid.

As nonlimiting examples of protective colloids, mention may be made of the cellulose derivatives such as the derivatives hydroxyethylcellulose, carboxyethylcellulose and methylcellulose, polyvinylpyrrolidone and polyvinylpyrrolidone copolymers, polyvinyl alcohols, more or less hydrolyzed as well as their copolymers, polymers of natural origin such as gelatin, xanthan gum or gum arabic, the alginates, pectins, starches and derivatives, casein as well as ionized polymers such as the polymers and copolymers of acrylic or methacrylic acid, the polymers bearing sulfonic or carboxylic acid groups or anhydrides thereof or cationized amine groups.

As noted above, simultaneous polymerization of the silicone and of the aminated resin is catalyzed at pH between 2 and 6, preferably between 3 and 5. Various metal or organometallic catalysts may be used for carrying out the polymerization reaction. We may mention, nonexhaustively, the compounds containing tin such as dibutyltin dilaurate or diacetate, tin octoate, the mineral salts of tin, and the compounds of platinum, zinc, zirconium, aluminum, or titanium including the titanates and the fluorides.

These compounds make it possible to lower significantly the level of residual alkoxy or silanol, which may be very interesting for certain applications and makes it, possible to avoid the reversion reactions.

The starting temperature depends on the ingredient to be encapsulated, but is determined in particular by the polymerization of the organic polymer. It is conceivably between 15° C. and 55° C., preferably between 20° C. and 50° C.

To stop polymerization, the temperature is often gradually increased to a value between 60 and 90° C., these values being only indicative as the optimal temperature ranges depend very much on the active substance that is encapsulated.

Departure of the alcohol formed during hydrolysis of the alkoxysilane groups is promoted by a high final temperature; this is all the more necessary because the aminated organic polymer forms a barrier and therefore impedes said departure, which means holding at high temperature for a longer time when this technology is compared to simple encapsulation with melamine-formaldehyde resin for example. The losses of volatile materials are generally compensated if necessary by supplying water during encapsulation.

At the end of the operation, the reaction mixture is preferably brought back to room temperature, where the microcapsules can be stored and used as they are, in the aqueous suspension. In fact, the media and conditions for use of the microcapsules mean that it is often preferable to bring the pH back up to values between about 5 and 8 with soda, potash, amines or any other means known by a person skilled in the art.

The microcapsules obtained by the process according to the invention may then be dried, separately or with other ingredients, in a spray tower, on a fluidized bed, by freeze-drying, or by any other means so that they can be used in dry compositions.

The lipophilic active substances that can be encapsulated according to the invention described are numerous, the only limitation being that they withstand the conditions of temperature and pH imposed during the operations of encapsulation and are compatible with alkoxysilanes or silicates.

The compounds of interest are those usually marketed, encapsulated by other techniques of the prior art.

Among the interesting active substances to be encapsulated, mention may notably be made of fatty acids and alcohols, organic solvents, hydrocarbons, esters, silicone fluids and gums, vegetable oils and vegetable extracts, in particular the products known for their cosmetic interest, such as vegetable oils and essential oils, reactive or non-reactive dyes, as well as dispersions of pigments, UV filters, vitamins and medically active molecules, perfumes and flavorings, insecticides and repellents, catalysts, phase-change materials, phenolic compounds, adhesives and chemical reagents, this list not being exhaustive.

The present invention also relates to the microcapsules prepared by the process described above, comprising a silicone polymer and an aminated organic polymer, bound together by polar, hydrogen or covalent bonds, making up the wall of the envelope of the microcapsules, used in formulations containing surfactants, more particularly the microcapsules containing an odorous molecule, such as a perfume, as the active ingredient.

The microcapsules according to the invention may be semipermeable or impervious. This may be achieved by a person skilled in the art by adjusting the polymerization conditions of the wall as well as the dimensional characteristics of the microcapsules such as the diameter and the wall thickness.

The weight ratio of the wall to the contents of the microcapsules may vary widely, for example between 5 and 50%, preferably between 10 and 30%, more preferably between 15 and 20%. If this ratio is too low, the wall is thin, porous and lacks mechanical strength and chemical resistance. If the ratio corresponding to the wall is too great (for example above 50%) the microcapsules are too solid, and can no longer release the active substance. Moreover, they are too expensive as they require a large amount of polymers.

The final dispersion of the microcapsules in the water of the reaction mixture generally contains from 30 to 50% of active substance contained within the microcapsules; it can be diluted or concentrated by the usual means, or else dried to be available in the form of a pulverulent powder (in this case the concentration of active substance may reach about 80%).

The microcapsules according to the present invention may be used in all applications where the microcapsules manufactured by the techniques of the prior art have been used to date: for example in the cosmetics industry (notably UV filters, vitamins, unsaturated oils, hydrophilic or lipophilic active substances of all categories, colorants, perfumes), in the paper industry (carbonless copying paper of the NCR type, papers for securities, tissues such as handkerchiefs, wipes, perfumed advertisements for example), in the textile industry (cosmetotextiles, perfumes, PCMs), in the leather industry, in pharmacy, in medicine, in the veterinary industry, in the field of adhesives, paints and coatings, as well as in the building sector.

The present, invention thus relates to the use of the microcapsules prepared by the process described above notably in liquid washing agents, washing powders or household and industrial detergents, in fabric conditioners or in shampoos, hair conditioners, toothpastes, liquid soaps, body cleansers or lotions.

The invention will now be illustrated by the nonlimiting examples given hereunder.

EXAMPLE 1: MICROCAPSULES CONTAINING A MOSQUITO REPELLENT

The following are put in an 800-cm$^3$ beaker maintained at 30° C., with stirring:

300 g of tap water 48.6 g of Lupasol PA 140 (BASF) (acrylamide: protective colloid)

52.5 g of a melamine-formaldehyde resin (Luracoll SD BASF)

The stirrer is equipped with a deflocculating turbine with a diameter of 7 cm. The stirring speed is increased to 900 rev/min. Then a homogeneous mixture of 216 g of Chinese citronella and 24 g of ethyl polysilicate (TES 40 Wacker) is emulsified in the aforesaid aqueous mixture.

To polymerize the whole, it is acidified with 11.1 g of 10% formic acid to a pH of about 3.5.

The temperature is maintained at 35° C. for 2 h, during which time the stirring speed is set at about 1500 rev/min so as to obtain an average microcapsule diameter of 6 µm.

Once this diameter is obtained, the speed is reduced to 1.200 rev/min and then the temperature is raised to 80° C. for 2.5 h for complete polymerization of the two layers. The emulsion is then cooled to 30° C., The formaldehyde is neutralized by slowly adding ammonia to pH 9.0.

Results: compared to the same microcapsules made without ethyl polysilicate, these microcapsules when spread on paper have a less strong odor, showing better hermeticity, and especially a lower level of formaldehyde.

EXAMPLE 2: MICROCAPSULES CONTAINING A MENTHOL PERFUME

The following were put in a 500-cm$^3$ beaker maintained at 35° C., with stirring:

110 g of tap water 16 g of Lupasol PA 140 (BASF)

15 g of a melamine-formaldehyde resin (Cymel 373 from Cytex)

The stirrer is equipped with a propeller with 5 straight blades with a diameter of 6 cm.

The stirring speed is increased to 750 rev/min and then a homogeneous mixture of 86 g of menthol perfume, 5.6 g of ethyl polysilicate (TES 40 Wacker), 2.8 g of methyltriethoxysilane and 1.2 g of MTMO (mercaptopropyltrimethoxysilane) is emulsified in the aforesaid aqueous mixture.

To polymerize the whole, it is acidified with 4.4 g of 10% formic acid; the pH is then 3.5.

The temperature is maintained at 35° C. for 2.5 h and then at 45° C. for 1 h, during which time the stirring speed is set at 1100 rev/min so as to obtain an average particle diameter of 15 µm, then it is decreased to 900 rev/min. The temperature of the reaction mixture is then raised to 80° C. for 3 h for complete polymerization of the 2 layers.

The emulsion is then cooled to 30° C. The formaldehyde is neutralized by slowly adding ammonia to pH 9.0.

Results: compared to the same microcapsules made without adding silane and silicate compounds to the lipophilic phase containing the perfume, these microcapsules spread on paper have a less strong odor, showing better hermeticity, and especially a lower level of formaldehyde.

EXAMPLE 3: MICROCAPSULES CONTAINING A PERFUME

1) Preparation of the Silicone Monomer A:

The following are mixed in a beaker protected from oxygen and moisture (circulation of dry nitrogen):
  0.01 mole of ETTMP 700 (ethoxylated trimethylolpropane tri-3-mercapto-propionate 700) sold by Bruno Bock, i.e. 7.08 g
  0.025 mole of glymo (gamma-glycidoxytrimethoxysilane), i.e. 5.9 g.

The whole is mixed and maintained at 60° C. for 10 h and then cooled to room temperature.

2) Encapsulation 111 g of Blue Wave perfumed expressions perfume is mixed so as to obtain a transparent solution with 6.0 g of silicone monomer A prepared previously and 14.8 g of ethyl polysilicate TES 40 from Wacker. This mixture will constitute the internal phase of the microcapsules.

130 g of water, 24 g of Lupasol PA140 from BASF (protective colloid) and 8.5 g of melamine-formaldehyde resin Beetle PT336 from BIP are then put in a beaker heated to 30° C.

The internal phase prepared previously is added to the aforesaid aqueous mixture and emulsified with stirring, the stainless-steel propeller with a diameter of 6 cm being rotated at 1200 rev/min, then 1.22 g of 20% nitric acid is added to obtain a pH of the reaction mixture of 4.15.

The temperature of 30° C. is maintained for 2 h, then it is heated at 40° C. for 30 min. Then 0.2 g of 20% hydrochloric acid is added and it is left for 1 h at 40° C.

During these steps the speed of the stirrer is lowered to 800 rev/min as soon as a diameter of 12 µm is reached.

The temperature is then raised to 80° C. for 6 h to finish the simultaneous polymerization of the two layers of polymer. The pH is then increased to 9.3 again with ammonia to lower the level of residual formaldehyde.

The microcapsules obtained have a lifetime in the fabric conditioners and the liquid washing agents greater than 6 months. The level of residual formaldehyde is of the order of 100 ppm.

EXAMPLE 4: MICROCAPSULES CONTAINING A PERFUME

1) Preparation of the Silicone Monomer: Same as Example 3

2) Encapsulation:

111 g of "Blue wave perfumed expressions" perfume is mixed so as to obtain a transparent solution with 5.0 g of the silicone monomer prepared previously and 14.8 g of ethyl polysilicate TES 40 from Wacker. This mixture will constitute the lipophilic internal phase of the microcapsules.

130 g of water, 20.2 g of Lupasol PA140 from BASF (protective colloid), 7.8 g of melamine-formaldehyde resin Beetle PT336 from BIP and 1.75 g of terephthalic aldehyde are put in a beaker heated to 30° C.

The lipophilic phase prepared previously is added to the aforesaid aqueous mixture and emulsified with stirring, the stainless-steel propeller with a diameter of 6 cm being rotated at 1200 rev/min, and then 1.15 g of 20% nitric acid is added to obtain a pH of the reaction mixture of 4.10.

The temperature of 30° C. is maintained for 2 h, and then the whole is heated at 40° C. for 30 min.

Then 0.8 g of xylitol powder and 1 g of melamine-formaldehyde resin Beetle PT336 from BIP are added, and then it is left for 1.5 h at 40° C.

During these steps the speed of the stirrer is lowered to 800 rev/min as soon as a diameter of 12 µm is reached.

The temperature is then raised to 80° C. for 6 h to finish the simultaneous polymerization of the two layers of polymers. Then the pH is increased to 9.3 again with ammonia to lower the level of residual formaldehyde.

The microcapsules obtained have a lifetime, in the fabric conditioners and the liquid washing agents, greater than 10 months. The level of residual formaldehyde is of the order of 90 ppm.

EXAMPLE 5: FORMALDEHYDE-FREE MICROCAPSULES CONTAINING A PERFUME

1) Preparation of the Silicone Prepolymer:

The following are mixed in a beaker protected from oxygen and moisture (circulation of dry nitrogen):
  0.1 mole of HMDI (hexamethylene diisocyanate), i.e. 16.8 g
  0.2 mole of MTMO (gamma-mercaptopropyl trimethoxysilane), i.e. 39.8 g.

The whole is mixed and maintained at 60° C. for 10 h and then cooled to room temperature (20° C. to 25° C.).

2) Encapsulation 111 g of "Blue wave perfumed expressions" perfume is mixed so as to obtain a transparent solution with 8.5 g of the silicone prepolymer prepared previously in 1) and 14.8 g of ethyl polysilicate TES 40 from Wacker. This mixture will constitute the lipophilic internal phase of the microcapsules.

The following were put in a 500-cm$^3$ beaker maintained at 45° C., with stirring:
  130 g of tap water
  1 g of hydroxyethylcellulose (250M of Aqualon)
  2 g of Lupasol PA 140 (BASF)
  2.7 g of melamine powder
  5.95 g of 40% glyoxal
  1.16 g of 50% glutaraldehyde
  and 6 g of 20% nitric acid.

The stirrer is equipped with a propeller with 5 straight blades with a diameter of 6 cm. The stirring speed is increased to 1600 rev/min and then the mixture prepared previously from the "Blue wave" perfume is emulsified in the aforesaid aqueous mixture. The pH is then 3.8.

The temperature is maintained at 45° C. for 2 h and then raised to 50° C. for 1 h, during which time the stirring speed is set at 1800 rev/min so as to obtain an average diameter of 10 µm, then it is decreased to 1300 rev/min.

0.5 g of Fixapret NF (BASF) is then added. The temperature is maintained at 50° C. for 1 h, and then raised to 80° C. for 6 h for complete polymerization of the 2 layers of polymers of the envelope of the microcapsules. The emulsion is then cooled to 30° C.

Then the pH is slowly increased again to 7.0 with potash lye.

Results: the microcapsules obtained have hermeticity performance comparable to the standard melamine-formaldehyde microcapsules but have a level of formaldehyde of 0 ppm and greater resistance to surfactants.

COMPARATIVE EXAMPLE 8

Performance of the Microcapsules in a Washing Liquid

The aim is to incorporate microcapsules in a washing liquid (Fabric washing liquid HC 0097/1.2), and evaluate the permeability of the microcapsules in this liquid medium.

Description of the Capsules Tested

Four types of microcapsules with the same "Blue" perfume are tested:

S: silicone microcapsules, prepared according to example 3 of French patent FR 2937243;

M: melamine-formaldehyde microcapsules made according to U.S. Pat. No. 4,406,816 example 1 (with perfume);

G: gelatin microcapsules made according to patent EP 0 674 942 B1 Example 1 (with perfume);

SM: two-layer microcapsules according to the present invention from example 3 above.

The characteristics of the microcapsules prepared are presented in Table 1 below:

TABLE 1

| Type | Internal reference | Average diameter | Formaldehyde ppm |
|---|---|---|---|
| S (comparative) | 4331 | 6 μm | 0 |
| SM (invention) | 4643 | 6.5 μm | 100 |
| M (comparative) | 4623 | 6.8 μm | 450 |
| G (comparative) | 4624 | 7 μm | 5 |

Procedure

The microcapsules with 35 wt % of active substance are incorporated in the washing liquid in a weight ratio of 5/95 and mixed using a spatula.

Each of the mixtures is observed with the naked eye and then with the microscope and its stability is monitored over time.

Results

After observation with the microscope and photographing, the observations relating to the different mixtures, immediately after incorporation in the washing liquid, are presented in Table 2 below:

TABLE 2

| Microcapsules | In "Fabric washing liquid" |
|---|---|
| S 4331 | Well dispersed but slightly deformed |
| SM 4643 | Well dispersed but some capsules stick together/ Some small agglomerates |
| M 4623 | Well dispersed/Rare agglomerates |
| G 4624 | Well dispersed |

A week after accelerated aging at 40° C., the mixtures are observed again and the olfactory intensity is evaluated: the greater the latter, the more the microcapsules have been degraded (see Table 3 below):

TABLE 3

| Microcapsules | Appearance of the washing liquid | Observation with the microscope | Intensity of the perfume |
|---|---|---|---|
| S 4331 | White spot/Very thick/ Beige color | Well dispersed but bruised | Strong odor |
| SM 4643 | Beige white color, good homogeneity | Fairly well dispersed | Very weak odor Barely perceptible |
| M 4623 | Homogeneous, white spot on the top/ Less thick/Beige white color | Well dispersed | Relatively weak odor, Very perceptible |
| G 4624 | Beige white color, good homogeneity | Well dispersed | Very strong odor |

Then the classification presented hereunder is undertaken, from the sample releasing the least perfume to that, which smells strongest in the beaker. The most impervious microcapsules having the best olfactory rendition correspond to the test with the least strong smell, as shown schematically in the following table 4:

TABLE 4

| Weak Olfactory Intensity | Strong Olfactory Intensity |
|---|---|
| Microcapsules Remaining Impervious | Microcapsules have become porous |
| SM 4643 < M 4623 < S 4331 < G 4624 | |

CONCLUSION

The double-walled SM microcapsules are the most impervious; they release less perfume than the other microcapsules as they were attacked less by the surfactants in the washing liquid. The "melamine" microcapsules M are moderately impervious, and in addition they have a very high level of formaldehyde. The "silicone" microcapsules S have little resistance in the solutions of surfactants. The "gelatin" microcapsules G are the ones that release most odor and that have therefore become the most porous.

The invention claimed is:

1. A process for manufacturing reservoir microcapsules, containing an active ingredient in a polymer-based envelope comprising the steps of:
   (i) dispersing at least one lipophilic active ingredient in an aqueous continuous phase, so as to form an emulsion or a dispersion of droplets of a oil-in-water type and
   (ii) polymerizing at least one precursor of the polymer in situ at the periphery of said droplets to form a double walled envelope of the microcapsules, enclosing the active ingredient,
   wherein the polymerization step (ii) is preceded by the introduction of one or more compounds having alkoxysilane groups into the lipophilic phase and the introduction of one or more aminated organic monomers and/or aminated organic prepolymers into the aqueous phase, wherein the one or more aminated organic monomers and/or aminated organic prepolymers comprises at least one group selected from melamine, urea, glycoluril, benzoguanamine, or dicyandiamide groups and one or more aldehydes, the one or more compounds having alkoxysilane groups and one or more aminated organic monomers and/or aminated organic prepolymers then being hydrolyzed and condensed in an acid medium to a silicone polymer and an aminated organic polymer, bound together by polar, hydrogen or covalent bonds, making up the double wall of the envelope of the microcapsules,
   said double walled envelope being made of a silicone polymer wall surrounded by a wall of aminated organic polymer,
   said polymerization of the one or more compounds having alkoxysilane groups and the one or more aminated organic monomers and/or aminated organic prepolymers being simultaneous when the one or more aminated organic monomers and/or aminated organic prepolymers are introduced with a delay relative to the one or more compounds having alkoxysilane groups allowing formation of the silicone polymer to start first.

2. The process as claimed in claim 1, wherein the silicone polymer and the aminated organic polymer, are formed simultaneously by acid catalysis at a pH between 2 and 6.

3. The process as claimed in claim 1, wherein the silicone polymer and the aminated organic polymer, are formed simultaneously by acid catalysis at a pH between 3 and 5, by adding at least one acid comprising nitric acid to the oil-in-water emulsion or dispersion.

4. The process as claimed in claim 1, wherein the aminated organic prepolymer is a melamine-formaldehyde and/or urea-formaldehyde resin.

5. The process as claimed in claim 1, wherein the aldehyde used for manufacturing the aminated organic prepolymer is selected from acetaldehyde, glyoxal, glutaraldehyde, or a mixture thereof, and/or one or more acetals of these aldehydes.

6. The process as claimed in claim 1, wherein the aminated organic polymer is copolymerized with aliphatic or aromatic hydroxylated monomers and/or aromatic aldehydes.

7. The process as claimed in claim 1, wherein the one or more compounds having alkoxysilane groups is/are selected from the compounds of formula (I) or (II) below:

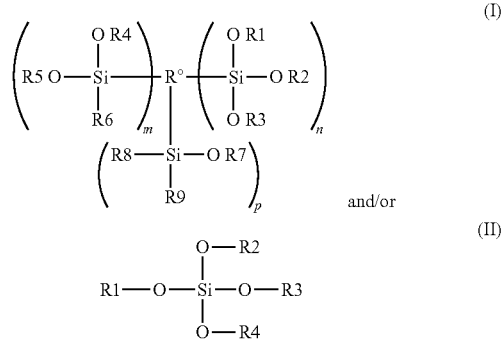

in which R1, R2, R3, R4, R5, R6, R7, R8, R9 are substituted or unsubstituted, linear or cyclic alkyl radicals, R° is an organic and/or silicone molecule, the groups between { } being joined to R° by a silicon atom and are present m, n, or p times, and m, n, p may be zero individually, but the sum m+n+p is at least equal to 1, wherein m+n+p is such that said compound remains liquid.

8. The process as claimed in claim 7, wherein the compound of formula (II) is selected from methyl polysilicate, ethyl polysilicate or a mixture thereof.

9. The process as claimed in claim 1, wherein the silicone polymer represents from 5 to 95% of the total weight of the polymers forming the double wall of the envelope of the microcapsule.

10. Microcapsules prepared by the process as claimed in claim 1, comprising a silicone polymer and an aminated organic polymer, bound together by polar, hydrogen or covalent bonds, making up the double wall of the envelope of the microcapsules, wherein said double-wall has a silicone polymer wall surrounded by an aminated organic polymer.

11. The microcapsules as claimed in claim 10, containing a perfume as the active ingredient.

12. A formulation containing a surfactant comprising: microcapsules prepared by the process as claimed in claim 1, wherein said double-wall of said microcapsules have a silicone polymer wall surrounded by an aminated organic polymer.

13. Liquid washing agents, washing powders or household and industrial detergents comprising:
microcapsules prepared by the process as claimed in claim 1, wherein said double-wall of said microcapsules have a silicone polymer wall surrounded by an aminated organic polymer.

14. Fabric conditioners comprising: microcapsules prepared by the process as claimed in claim 1, wherein said double-wall of said microcapsules have a silicone polymer wall surrounded by an aminated organic polymer.

15. Shampoos, hair conditioners, toothpastes, liquid soaps, body cleansers or lotions, comprising: microcapsules prepared by the process as claimed in claim 1, wherein said double-wall of said microcapsules have a silicone polymer wall surrounded by an aminated organic polymer.

16. The process as claimed in claim 1, wherein the one or more compounds having alkoxysilane groups and the one or more aminated organic monomers and/or aminated organic prepolymers are simultaneously hydrolyzed and condensed.

17. The process as claimed in claim 1, wherein the silicone polymer is 10 to 90% of the total weight of the polymers forming the double wall of the envelope of the microcapsule.

18. The process as claimed in claim 1, wherein the silicone polymer is 15 to 85% of the total weight of the polymers forming the double wall of the envelope of the microcapsule.

* * * * *